US009855360B2

(12) United States Patent
Broyles et al.

(10) Patent No.: US 9,855,360 B2
(45) Date of Patent: Jan. 2, 2018

(54) AROMATIC ADHESIVE-BACKED TAB AND METHOD OF USING SAME

(75) Inventors: Mark Broyles, Plainville, CT (US); Rita Chew, Everett, WA (US)

(73) Assignee: BEEKLEY CORPORATION, Bristol, CT (US)

( * ) Notice: Subject to any disclaimer, the term of this patent is extended or adjusted under 35 U.S.C. 154(b) by 1558 days.

(21) Appl. No.: 13/549,082

(22) Filed: Jul. 13, 2012

(65) Prior Publication Data

US 2013/0015258 A1  Jan. 17, 2013

Related U.S. Application Data

(60) Provisional application No. 61/507,485, filed on Jul. 13, 2011.

(51) Int. Cl.
 *A61L 9/00*  (2006.01)
 *A61L 9/04*  (2006.01)
 *A61L 9/013* (2006.01)

(52) U.S. Cl.
 CPC ............. *A61L 9/042* (2013.01); *A61L 9/013* (2013.01)

(58) Field of Classification Search
 CPC ...................................................... A61L 9/042
 See application file for complete search history.

(56) References Cited

U.S. PATENT DOCUMENTS

| 2,615,754 | A |   | 10/1952 | Lindenberg |
| 4,277,024 | A | * | 7/1981  | Spector ............... A01M 29/12 206/466 |
| 4,283,011 | A |   | 8/1981  | Spector |
| 4,647,433 | A |   | 3/1987  | Spector |
| 4,744,514 | A |   | 5/1988  | Gadona |
| 4,874,129 | A |   | 10/1989 | DiSapio et al. |
| 4,880,690 | A |   | 11/1989 | Szycher et al. |
| 5,071,704 | A | * | 12/1991 | Fischel-Ghodsian A01M 1/2055 261/DIG. 88 |
| 5,136,640 | A |   | 8/1992  | Kim |
| 5,242,521 | A |   | 9/1993  | Hibsch et al. |
| 5,389,174 | A |   | 2/1995  | Hibsch et al. |
| 5,391,420 | A | * | 2/1995  | Bootman ............... A45D 37/00 206/213.1 |
| 5,395,047 | A |   | 3/1995  | Pendergrass, Jr. |
| 5,399,404 | A |   | 3/1995  | Laughlin et al. |
| 5,439,172 | A |   | 8/1995  | Comyn et al. |
| 5,637,401 | A |   | 6/1997  | Berman et al. |

(Continued)

FOREIGN PATENT DOCUMENTS

JP       09076376 A   *   3/1997

OTHER PUBLICATIONS

Qiao et al (Molecules 2008, 13, 1333-1344; DOI: 10.3390/molecules13061333).*

(Continued)

*Primary Examiner* — Benjamin Packard
(74) *Attorney, Agent, or Firm* — McCarter & English, LLP

(57) ABSTRACT

A scent-releasing strip includes a release liner and a plurality of tab units coupled to the liner. Each of the plurality of tab units includes a sealed pouch having a pad dosed with at least one scent-emitting substance. The scent may induce a physiological effect. The sealed pouch is disposed on a base label. The pad may be an aroma-containing pad that includes at least one of an oil or other substance that emits a desired fragrance.

38 Claims, 6 Drawing Sheets

(56) References Cited

U.S. PATENT DOCUMENTS

| | | |
|---|---|---|
| 5,782,409 A | 7/1998 | Paul |
| 5,817,385 A | 10/1998 | Stanislav |
| 5,885,701 A | 3/1999 | Berman et al. |
| 6,162,457 A | 12/2000 | Martz |
| 6,244,265 B1 | 6/2001 | Cronk et al. |
| 6,276,360 B1 | 8/2001 | Cronk et al. |
| 6,364,097 B1 | 4/2002 | Whitaker et al. |
| 6,537,308 B2 | 3/2003 | Burkhart |
| 6,723,671 B2 | 4/2004 | Zolotarsky et al. |
| 6,746,750 B1 | 6/2004 | Bishopp |
| 6,755,350 B2 | 6/2004 | Rochford et al. |
| 6,769,428 B2 | 8/2004 | Cronk et al. |
| 7,354,667 B1 | 4/2008 | Knapp |
| 7,390,935 B1 | 6/2008 | Theno |
| 2005/0100566 A1 | 5/2005 | Morikane et al. |
| 2005/0169973 A1 | 8/2005 | Kim |
| 2006/0006301 A1 | 1/2006 | Turi et al. |
| 2006/0144506 A1 | 7/2006 | Ynzunza |
| 2006/0191290 A1 | 8/2006 | Chesne |
| 2006/0246265 A1* | 11/2006 | Rogers .................. B41M 3/006 428/195.1 |
| 2007/0006614 A1 | 1/2007 | Martz |
| 2007/0105977 A1 | 5/2007 | Gabriel |
| 2007/0138326 A1* | 6/2007 | Hu .................. A01M 1/2038 239/690 |
| 2007/0271716 A1 | 11/2007 | Spector |
| 2010/0003294 A1 | 1/2010 | Klausen et al. |

OTHER PUBLICATIONS

Redd, W. H., et al., "Fragrance Administration to Reduce Anxiety During MR Imaging", Journal of Magnetic Resonance Imaging, Jul./Aug. 1994, pp. 623-626, vol. 4, Issue 4.

Meléndez, J. Carlos, et al., "Anxiety-Related Reactions Associated with Magnetic Resonance Imaging Examinations", JAMA, Aug. 11, 1993, pp. 745-747, vol. 270, No. 6.

* cited by examiner

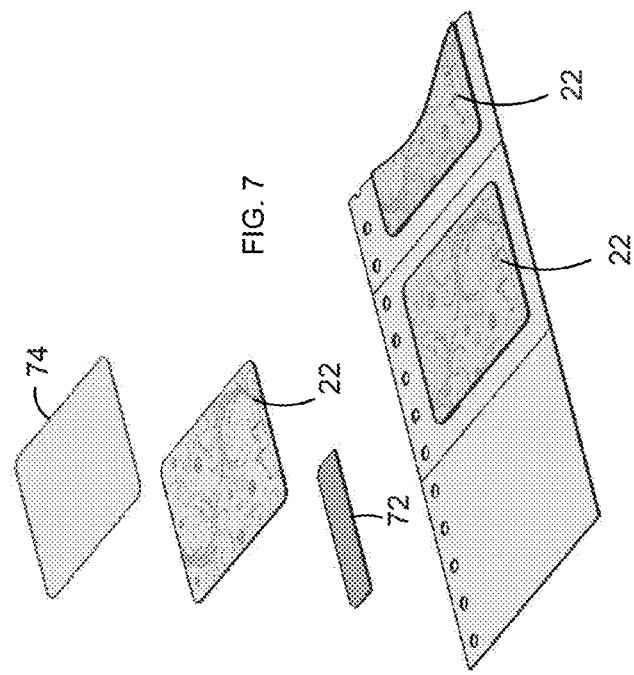
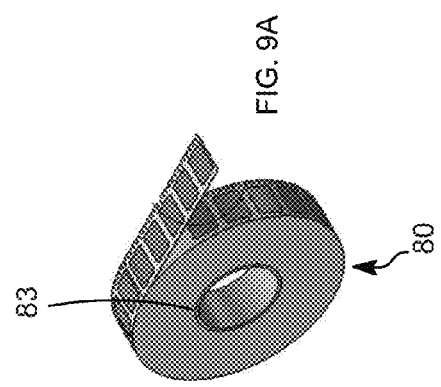

AROMATIC ADHESIVE-BACKED TAB AND METHOD OF USING SAME

CROSS REFERENCE TO RELATED APPLICATIONS

This application claims the benefit under 35 U.S.C. §119(e) of similarly-titled U.S. Provisional Application No. 61/507,485, filed Jul. 13, 2011, the contents of which are incorporated by reference in its entirety as if fully set forth herein.

FIELD OF THE INVENTION

The present invention relates generally to the field of aroma-releasing tabs and, more particularly, to tabs that are pleasing to the senses or having a desired physiological effect. The invention further relates to a method of using aroma-releasing tabs in connection with medical procedures, imaging, examinations, or other non-medical uses.

BACKGROUND OF THE INVENTION

To convey pertinent information on radiographic film, radiologists and technicians frequently use markers that absorb x-rays and cast a shadow when placed within the x-ray exposure field. Such markers are positioned either directly on a patient undergoing radiographic examination or on a cassette holding the radiographic film.

For example, right and left markers are routinely used to designate the anatomical orientation of the patient or to identify a particular extremity being examined. Markers are also used in trauma cases to localize the trauma site by placing the marker on the skin surface at the appropriate location prior to x-ray exposure. Further, markers are often placed on the surface of the examination table or a film cassette, within the exposure field but outside the imaged area of the patient, to convey the patient's physical orientation in relationship to the x-ray beam or the film, e.g., erect, prone, supine or decubitus.

During a medical procedure or examination, a patient may be nervous or uncomfortable. It would therefore be desirable to provide means for calming a patient during a medical procedure or examination. In addition, certain medical procedures use medicines or chemicals that have unpleasant smells, e.g., sterilants. Thus, it would also be desirable to counter act such smells.

In addition, it would be desirable in many situations, including non-medical situations, to provide a counter to unpleasant smells, or to provide a pleasant smell.

It is an object of the invention to overcome one or more of the above-described drawbacks and/or disadvantages of the prior art.

SUMMARY OF THE INVENTION

According to one aspect of the invention, scent-releasing labels or tabs are applied to a surface, for example, a user's skin or clothing to produce a pleasant fragrance in order to achieve a desired effect such as releasing a pleasant aroma, producing a calming effect or reducing nausea. The positive effects of a label may be particularly advantageous for use in connection with medical procedures, such as during mammogram, MRIs, other imaging procedures, needle injections and IV procedures. However, those skilled in the art should appreciate that the invention can be utilized in various other, non-medical circumstances.

In one aspect, an aromatic adhesive-backed tab or pad selectively emits an aroma. In some embodiments, a plurality of aroma tabs are releasably mounted on a liner provided in roll form. In some embodiments, each aroma tab includes an adhesive-backed label that is releasably attached to the release liner or strip, an absorbent pad that is impregnated or otherwise includes thereon an oil, 100% pure essential oil, or other substance that emits a desired fragrance, and a plastic pouch that hermetically seals the pad and fragrance-emitting substance in a chamber of the pouch until the tab is ready for use. In further embodiments, the liner contains perforations or a plurality of perforations so that a portion of the liner containing one or more aroma tabs may be separated from the liner.

In some embodiments, one end of the absorbent pad is secured to the pouch, such as by heat sealing, and the pouch is attached on the same end, such as by an adhesive, to the base label. The pouch may further include tear notches, frangible portions, edge slits, or like features that allow a user to tear open the pouch at the notches to remove a portion of the pouch surrounding the pad that is not attached to the base label and, in turn, expose the pad and fragrance-emitting substance. When the pouch is torn away, the fragrance-emitting substance emits a desired fragrance. The amount of oil or other fragrance-emitting substance is determined to provide a desired strength of fragrance for a predetermined period of time, such as at least the amount of time required for a medical procedure during which the tab is worn (e.g., about 2 to 3 hours). The adhesive-backed side of the label allows it to be releasably attached to a user's skin or clothing. The label includes an adhesive-free portion to facilitate removal from the liner and from the person's skin or clothing. In certain embodiments, the label is a foam material, so as to be comfortable when attached to the user and pleasant to the touch. In further embodiments, the foam provides a barrier between the pad and the user's skin or clothing, preventing direct contact between the pad and skin or clothing. Certain patients may be sensitive or allergic to the materials of or oils/fragrance in the pad.

One advantage of the proposed aromatic adhesive-backed tab is that it can be selectively positioned without irritating a user's skin or damaging a user's clothing, and also can be selectively activated to release an aroma at a desired time or for a desired duration. In at least some embodiments, the proposed aromatic adhesive-backed tab emits an aroma that is either pleasing to the senses or otherwise has a desired effect on the person wearing the label, such as reducing nausea or calming nerves. This is particularly advantageous for use in connection with medical procedures, such as during mammograms, MRI, other imaging procedures, needle injections, or IV procedures.

Other objects and advantages of the present invention and/or of the currently disclosed embodiments thereof will become more readily apparent in view of the following detailed description of various embodiments and accompanying drawings.

BRIEF DESCRIPTION OF THE FIGURES

FIG. 7 is a schematic partially exploded perspective view of base labels coupled to a liner strip;

FIG. 9A is a schematic perspective view of a plurality of aroma tab assemblies;

DETAILED DESCRIPTION OF EMBODIMENTS OF THE INVENTION

Figure 1:
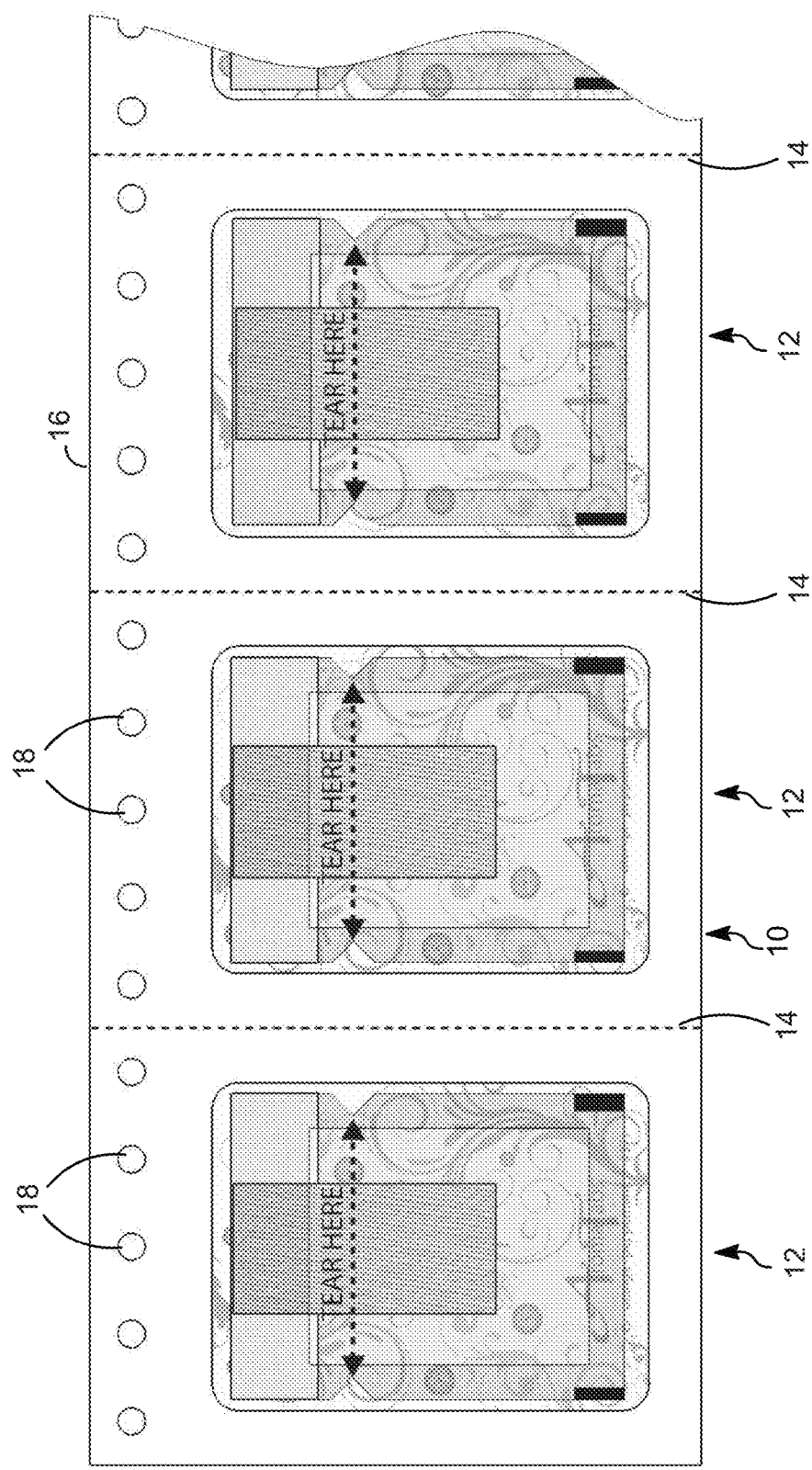
FIG. 1 is a schematic top view of one embodiment of an aroma tab strip including a plurality of individual tab units on a liner.
Figure 2:
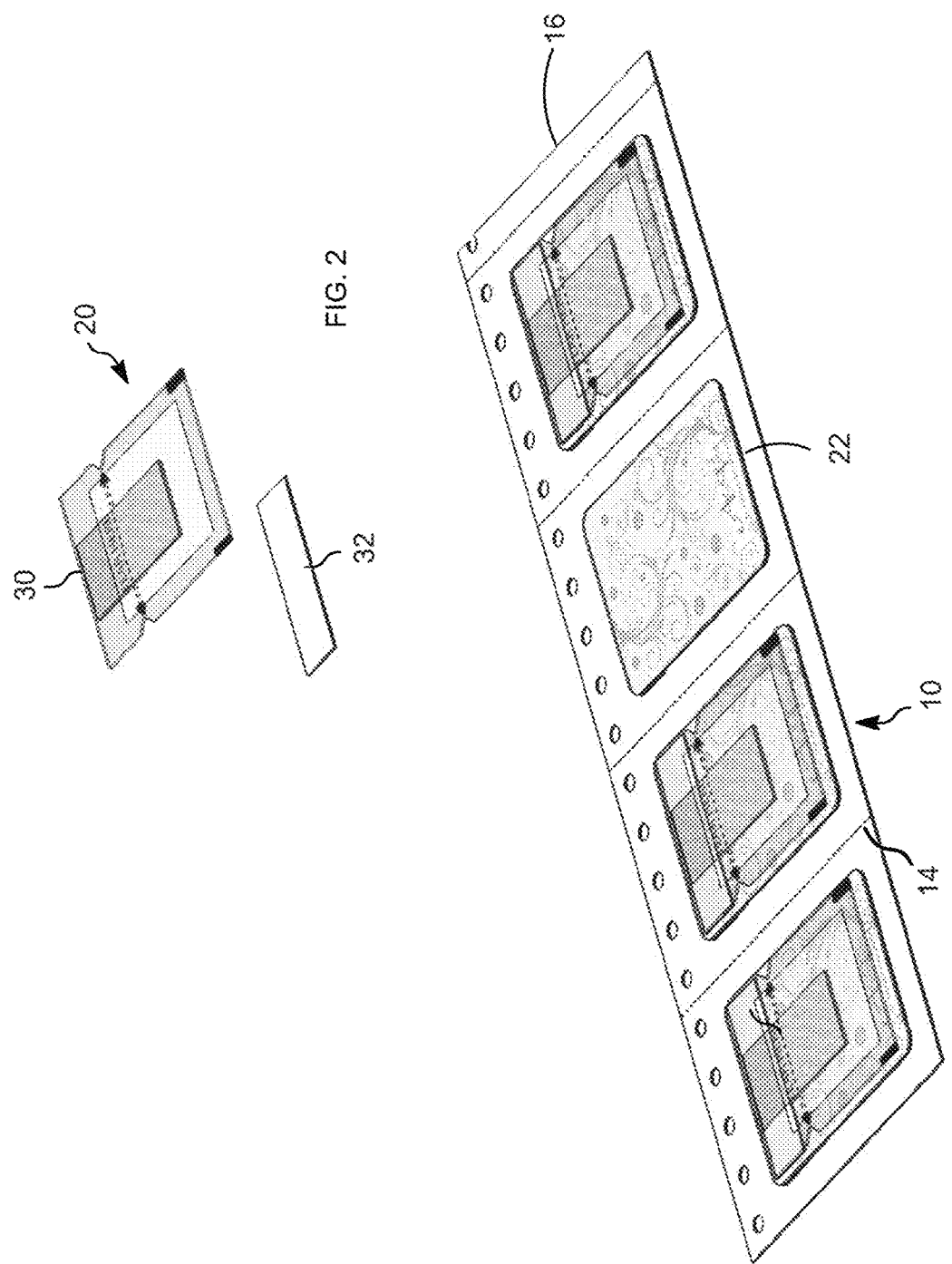
FIG. 2 is a schematic partially exploded perspective view of the aroma tab strip of FIG. 1.

As seen in FIG. 1 and FIG. 2, an aroma tab strip 10 has a liner 16 that includes a plurality of individual tabs or tab units 12. In some embodiments, the tab strip 10 is perforated 14, with the perforations 14 located between adjacent tab units 12. In such embodiments, each individual tab unit 12 is separable from an adjacent unit via an interceding perforation 14. The perforation 14 can be formed of any scoremark, slit, indentation, or area or line of weakness useful for cutting, tearing or otherwise decoupling a section of the tab strip 10 containing an individual tab unit 12 from the aroma tab strip 10. During use, a user, physician or other healthcare provider is thus able to tear or remove one or more individual tab units 12 from the rest of the aroma tab strip 10 depending on the number of tab units 12 desired. It will be understood that in other embodiments the perforations 14 may be otherwise configured to form units of two, three, four or any other number or grouping of individual tab units 12 as desired by the user and/or healthcare provider. The aroma tab strip 10 further includes a plurality of tractor holes 18 useful in handling and transport during manufacturing.

As can be seen in FIG. 2, each individual tab unit 12 has a sealed pouch 20, disposed on a base label 22, which is removably coupled to a liner 16. In some embodiments, the liner 16 is formed of a film or other appropriate material that is coated or covered on one or both sides to provide an appropriate surface for tactility, durability, printing or other desired purposes. Appropriate materials include, but are not limited to silicone coating or polyester laminate films. In at least some embodiments, the base label 22 is a polyethylene film with polyester laminate.

In some embodiments, the base label 22 is formed of a polyethylene foam such as MacTac™-6563 (two-sided approximately ⅟₃₂ inch thick foam tape) or other suitable substitute. The base label 22 may be disposed or coupled to the liner 16 at predetermined increments. As seen in FIGS. 1 and 2, a sealed pouch 20 is coupled to the base label 22 as will be described in greater detail below with reference to FIGS. 3 and 5.

Figure 3:
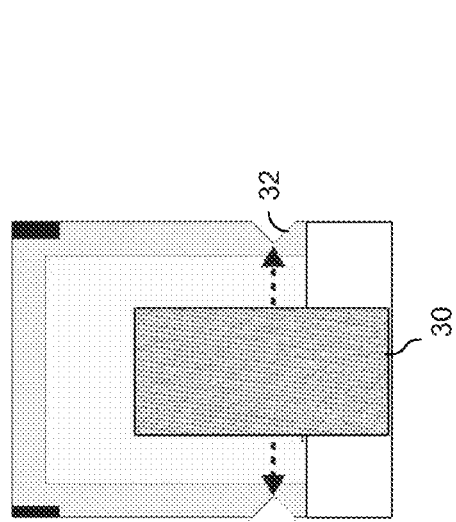
FIG. 3 is a schematic top view of sealed pouch including an aroma-containing pad of FIG. 1.
Figure 4:
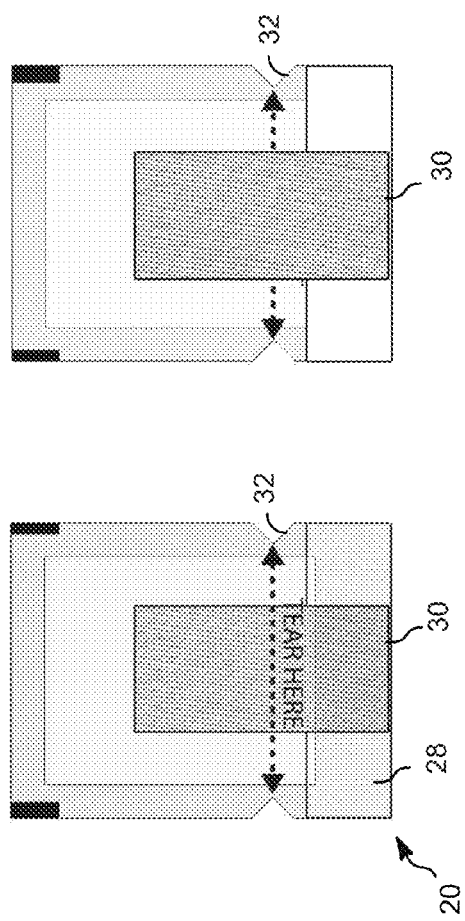
FIG. 4 is a schematic bottom view of the sealed pouch and aroma-containing pad of FIG. 1.

As seen in FIG. 3, the sealed pouch 20 includes an aroma-containing pad 30. The pouch 20 may be constructed of any suitable metal-free material and include any material such as PET/ADH/EVOH (Ethylene Vinyl Alcohol). The plastic pouch 20 may act to hermetically seal the pad 30 and fragrance-emitting substance in a chamber of the pouch until the tab is ready for use. This avoids the drying or dissipation of the scent or fragrance of the pad 30 until the pad 30 is ready for use. In some embodiments, the material is capable of being heat-sealed. In at least some embodiments, the material is capable of providing a water, vapor and/or air barrier. In the embodiment depicted in FIG. 3, the pouch 20 is a substantially rectangular packet including three sealed edges and including a fourth edge for accepting the pad 30 therein, but can be formed of any shape, size or configuration suitable for enclosing a pad 30. As seen in FIGS. 3 and 4, with the pad 30 securely positioned inside the pouch 20, a cross seal or bar seal 28 may be formed across the one end of the pouch 20 to anchor the end of the pad 30 in the pouch 20. In at least some embodiments, one end of the absorbent pad 30 is heat sealed to the pouch 20, and the pouch 20 is coupled in any manner (e.g., adhesively attached) to the same end to the base label 22.

The pad 30 can be configured in any shape, color and/or size that is capable of fitting within pouch 20. In some embodiments, the pad 30 is of a complementary or similar shape to the pouch 20. The pad 30 may be formed as an absorbent pad for receiving a fragrance, a dye or some other liquid. Any suitable absorbent/emitting material may be used as will be appreciated by those of ordinary skill in the art.

The pad 30 is impregnated with or otherwise includes thereon an oil or other substance that emits a desired fragrance or scent. For example, in at least some embodiments, the pad 30 is dosed with about 0.15 to about 0.20 ml of an orange/peppermint scent, with a ratio and/or concentration of oils as desired. In other embodiments, the pad 30 is dosed with about 0.15 ml of a lavender/sandalwood scent, again with a ratio and/or concentration of oils as desired. In various embodiments, these are 100% pure essential oils. The amount of oil or fragrance-emitting substance can be chosen to provide a scent for a predetermined period of time. For example, an effective amount may be used so that the fragrance lasts for two, three, four or five hours. In at least some embodiments, the effective amount is chosen to coincide with the duration a medical procedure (e.g., the fragrance lasts as long as a typical mammogram, MRI, other imaging procedure, needle injection, or IV procedure).

One or more dyes may also be added to the fragrance as desired for aesthetics. In some embodiments, the color is selected to compliment the selected fragrance, aroma, or scent. For example, in some embodiments, utilizing an orange fragrance, an orange-colored dye is used. In other embodiments where Lavender and/or Sandalwood is used, lavender-colored dye is used. The dye may also be selected or chosen based on the desired color. As will be appreciated by those of ordinary skill in the art, a sufficient amount and/or concentration of dye is used to provide the desired indication. In at least some embodiments, for example, the amount of dye is between, for example, about 0.15 ml to about 0.7 ml per about 100 ml of oil.

If a scent or fragrance is used, it may be chosen based on the desired physiological effect on the user. The fragrance can be chosen, for example, based on a scent or smell that provides a calming effect on the user or a scent that aids in alertness. The fragrance may also be chosen from any fragrance or scent that provides relief from nausea.

As is present in the embodiments of FIGS. 3 and 4, one or more notches 32 are formed in at least a side of the pouch 20, whose function and use are described below with reference to FIG. 6. In the embodiments of FIGS. 3 and 4, the notches 32 are triangular-shaped cutouts that facilitate a lateral tear across the face of the pouch 20 to release the pad 30 from therein. It will be understood that instead of triangular cutouts, the notches 32 may instead be formed of slits or other incisions or weakened portions for facilitating the tearing or opening of the pouch 20. The sealed pouch 20 including the pad 30 is coupled to the base label 22.

Figure 5:
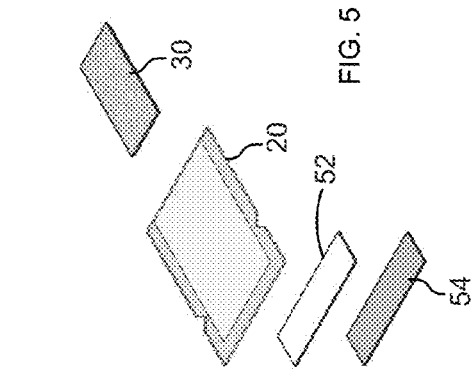
FIG. 5 is a schematic exploded perspective view of a pouch and pad.

Referring to FIG. 5 the pad 30 is positioned within the pouch 20 and cross-sealed. The pouch 20 includes a pouch bond 52 configured to couple the pouch 20 to the base label 22 or other surface. In at least some embodiments, the pouch bond 52 is an adhesive layer. In some embodiments, the pouch bond 52 includes a portion of double-sided tape configured to couple the backside of the pouch 20 to the base label 22. It will be understood that the pouch bond 52 can be any device or means to couple the pouch 20 to the label 22, e.g. staple, glue, heat, welding thereon. In embodiments where the pouch bond 52 includes double-sided tape, an optional liner 54 may be coupled to one side of the pouch bond 52 prior to assembly to the label 22 to protect the exposed adhesive and/or tape until the part is ready for assembly to the base label 22. When the liner 54 is removed, the pouch connector 52 will function to adhere the pouch 20 to the base label 22.

Figure 6:
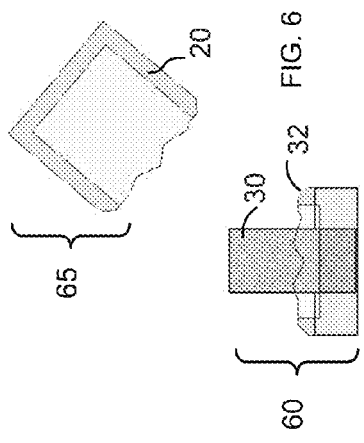
FIG. 6 is a schematic view of a pouch and pad assembly after the pouch is torn open to expose the absorbent pad.

FIG. 6 is a schematic view of a pouch and pad assembly after the pouch is torn open to expose the absorbent pad 30. As can be appreciated from FIG. 6, the pouch 20 is torn at notches 32, across the width of the pouch 20 so as to remove a tear-away portion 65 of the pouch 20 and expose at least a portion of the pad 30. This permits the scent to emanate from the pad. With the pouch 20 torn, the lower portion 60 of the pouch 20 still anchors the pad 30 within the pouch 20. Thus, the plastic pouch 20 acts to hermetically seal the pad 30 and fragrance-emitting substance in a chamber of the pouch until the tab is ready for use. This avoids the drying or dissipation of the scent or fragrance of the pad 30 until the pad 30 is ready for use.

Referring to FIG. 7, the base label 22 is releasably attached to the liner. In some embodiments, the base label 22 is formed of polyethylene film such as Flexcon™ PE 650 and an optional polyester laminate 74. The base label 22 may include a print for aesthetics with a predetermined design or artwork. The laminate 74 aids in protecting the ink of the design or artwork. In some embodiments, the label 22 is adhesive-backed for releasable attachment to the release liner or strip 16. In others, the adhesive allows the user to remove the label from the liner (including pouch/pad in relevant embodiments) without damage to same, but is strong enough to prevent it from falling off. The adhesive may be removably adhereable to the skin of the user. The adhesive can also be strong enough to remain in position while the user is moving. In various embodiments, the adhesive is removable without causing excess discomfort to the user. In some embodiments, a portion of the back of the label does not have adhesive so that such portion may be easily grasped and lifted from the liner by the user to facilitate removal of the remaining adhesive-backed portion. In yet other embodiments, such as depicted in FIG. 7, a liner strip 72 is joined to the bottom of base label 22 in order to provide an adhesive-free area so that the individual tab unit 12 may be removed from the strip 10 and attached to a surface of the skin or clothing of the user. The adhesive-backed side of the base label 22 facilitates the attachment to a user's skin or clothing.

Thus, the present aromatic adhesive-backed tab can be selectively positioned without irritating a user's skin or damaging a user's clothing, and can also be selectively activated to release an aroma at a desired time. The aromatic adhesive-backed tab may thus emit an aroma that is either pleasing to the senses or otherwise has a desired effect on the person wearing the label, such as reducing nausea or calming nerves. In some embodiments, the adhesive-backed tab is placed on the face, neck, shoulder, chest, arm or back of the patient. In at lease some embodiments, the tab is placed on a body part that is not overly contoured and that is close enough to the patient's nose so that the scent is effective. The tab also may be placed on an article of clothing or accessory of the patient.

It will be understood that the pad may be directly attachable to the user. In some embodiments, only a pad is provided with adhesive to attach to the patient. In some other embodiments, the pad is provided in a pouch as described above and removed from the pouch for application.

In some embodiments, the adhesive-backed tab includes a first scented layer that is removably attachable to the user. The adhesive-backed tab may further include a second layer, the second layer being attached to the first layer. The second layer may be configured for being removably attached to the user. In yet further embodiments, the tab includes a pouch attached to the second layer and at least partially enclosing the first layer therein.

Figure 8B:
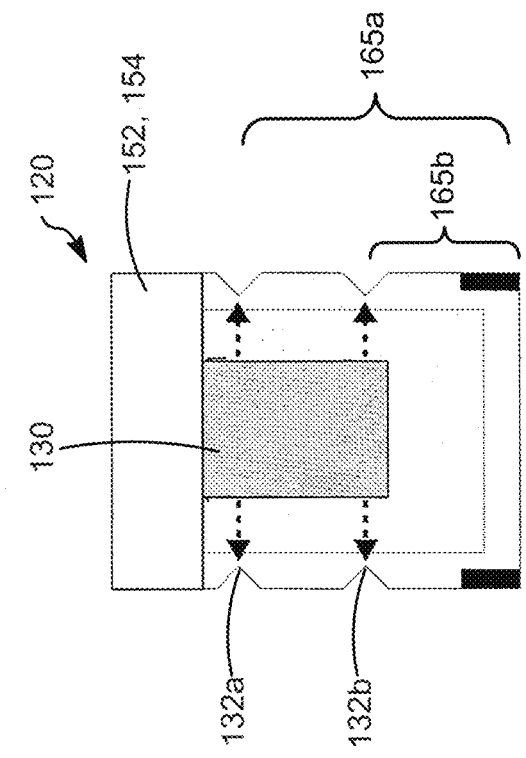
FIG. 8B is a schematic bottom view of the sealed pouch and aroma-containing pad of FIG. 8A.
Figure 8A:
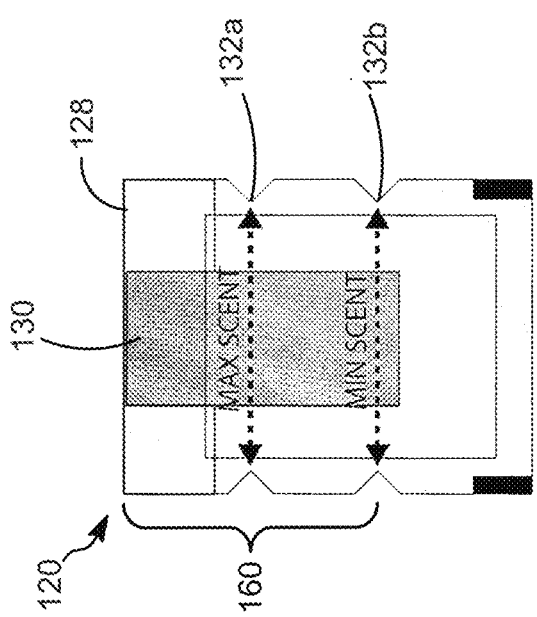
FIG. 8A is a schematic top view of another embodiment of a sealed pouch including an aroma-containing pad.

In FIGS. 8A and 8B, another sealed pouch is indicated generally by the reference numeral 120. The pouch 120 is substantially similar to the pouch 20 described above with reference to FIGS. 1-7, and may be used in a similar manner, and therefore like reference numerals preceded by the numeral "1" are used to indicate like elements. A primary difference of the pouch 120 in comparison to the pouch 20 described above is that it has two sets of notches 132a, 132b located at different positions along the pad 130. These notches 132a, 132b permit differently-sized tear-away portions 165a, 165b to be removed from the pouch 120, thereby exposing differently-sized portions of the pad 130. The amount of exposed pad 130 affects the amount, level or strength of scent released from the pad 130. Accordingly, a user may select the portion of the pouch 120 to remove and/or the amount of pad 130 to expose, to control or vary the amount, level or strength of emanated scent as desired.

In the illustrated embodiment, notches 132b facilitate the removal of a relatively smaller tear-away portion 165b, exposing a relatively smaller portion of the pad 130. This amount of exposed pad 130 provides a relatively lower or "MIN SCENT" level of scent release from the pad 130. In contrast, notches 132a facilitate the removal of a relatively larger tear-away portion 165a, exposing a relatively larger portion of the pad 130. This amount of exposed pad 130 provides a relatively higher or "MAX SCENT" level of scent release from the pad 130.

In addition to controlling the amount, level or strength of scent released, the multiple tear-away portions 165a, 165b may be used to control the timing of scent release or to extend the period of scent release. For example, if portion 165b is removed from the pouch 120, the exposed portion 130 will emanate scent, which will, over time, dissipate. However, the portion of the pad 130 that is still covered by the pouch 120 will retain at least a portion of its scent for a longer time period than the portion of the pad 130 completely exposed by the removal of portion 165b. Then, the remainder of tear-away portion 165a that is still attached to the pouch 120 can be removed, exposing an additional portion of the pad 130.

Though the embodiment of FIGS. 8A and 8B have two sets of notches at the indicated locations, those of ordinary skill in the art should appreciate that the notches may be at other positions on the pouch 120, and the pouch 120 may have additional sets of notches to provide additional tear-away portions exposing greater or lesser portions of the pad 130, as may be desirable. In this manner, even greater control of the amount, level, strength or timing of scent release can be achieved.

Figure 9B:
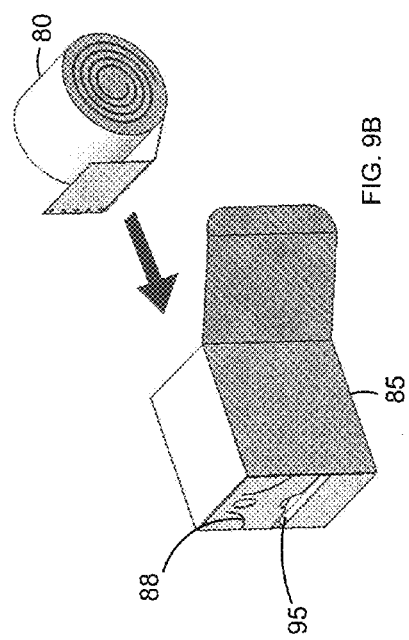
FIG. 9B is a schematic perspective view of the roll of FIG. 9A being loaded into a box.
Figure 10:
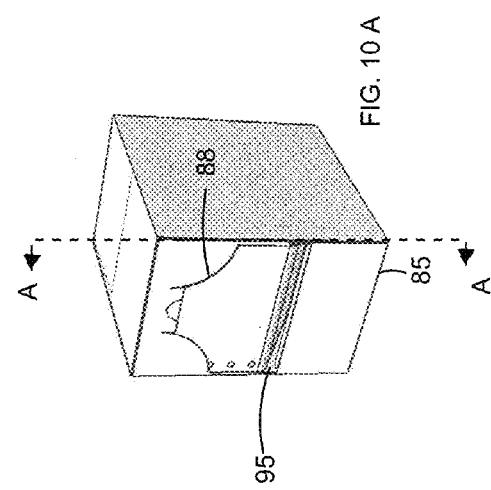

With the individual tab units 12 containing pouches 20, 120 assembled to the strip 10, and as depicted in FIG. 9A, a roll 80 is formed for ease of storage and shipment. As seen in FIG. 9A, the roll 80 includes a core 83 to facilitate rolling the strip 10. In some embodiments, the core 83 is an approximately 6-inch core. In some embodiments, the roll 80 is assembled with a diameter within the range of about 12 inches to about 20 inches. In at least some embodiments, the roll diameter is about 16 inches or less. The roll 80 is loaded into a box 85 as seen in the embodiments of FIG. 9B. In alternate embodiments, the roll 80 is formed so that the aroma tabs are located on the inside or outside of the roll as desired.

Figure 10:
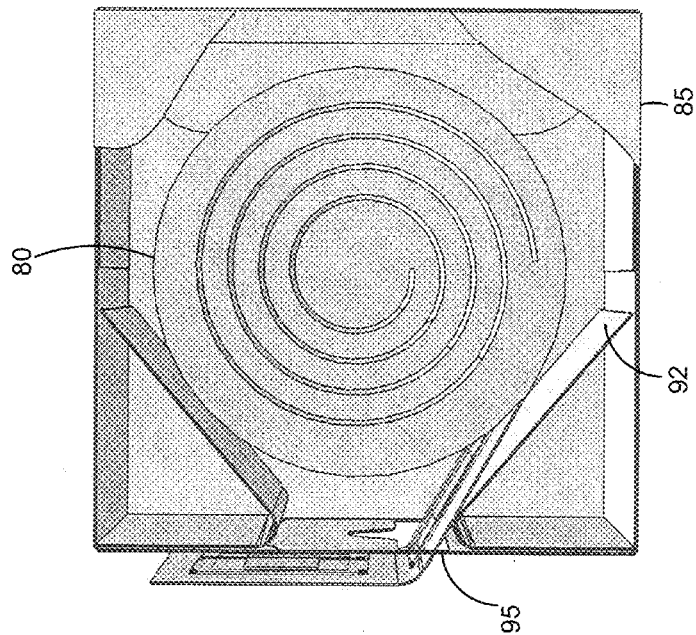
FIG. 10A is a schematic perspective view of the box of FIG. 9B containing a single roll.
FIG. 10B is a schematic cross-sectional view of the box of FIG. 10A containing the roll of aroma tab strips along lines A-A.

As seen in FIG. 10A, the box 85 has an aperture 95 through which the end of the roll 80 extends for access and dispensing by a user. The roll 80 is disposed or placed in the box 85 with the tractor holes 18 position to the left of the box 85, but in alternate embodiments, the tractor rates 18 may be positioned to the right side, on both sides, or in another location. The box 85 includes one or more cuts 88 in the front of the box 85 for tucking away the end of the roll 80 to prevent undesired unrolling or damage. In at least some embodiments, the cuts 88 in the front of the box 85 include a pair of semi-circular cuts for tucking away the end of the roll 80, although it will be understood that the cuts also may include horizontal, vertical or angled slits or curves for tucking in the end of the roll 80, or any combination thereof. As seen in FIG. 10B, the box 85 includes a pair of roll guide ramps 92 to facilitate unwinding the roll 80 when the user requires additional tabs. It will be understood that the box can, in other embodiments, have fewer or more guide ramps or no guide ramps.

While certain embodiments have been shown and described, various modifications and substitutions may be made without departing from the spirit and scope of the invention. For example, the size and shape of the tab may be modified as desired. The location or placement of the tab on the skin or clothing of the user also may be modified accordingly. For example, the notches may take any of numerous different shapes that are currently known, or that later become known, such as v-shapes or arcuate shapes. In addition, the device may include in addition to, or instead of notches, any of numerous other features that facilitate tearing or otherwise opening the pouch to expose the pad and its scent-emitting substance to ambient air, such as one or more edge slits, frangible portions, or seams. The tab units can be made of any of numerous different materials and/or in any of numerous different shapes or configurations that are currently known, or that later become known. Similarly, the fragrance or scent-emitting substance and the mechanism for holding, storing, and/or releasing the fragrance or scent-emitting substance, may take any of numerous different forms or configurations that are currently known, or that later become known. Accordingly, it is to be understood that the present invention has been described by way of example and not by limitations.

What is claimed is:

1. A device comprising:
    a liner; and
    a plurality of tabs coupled to the liner, each tab comprising a label attached directly to the liner, and each tab further comprising a sealed pouch disposed on the label and including therein a pad with at least one scent-emitting substance thereon.

2. A device as defined in claim 1, wherein the scent-emitting substance is an oil.

3. A device as defined in claim 1, wherein the scent-emitting substance is a 100% pure essential oil.

4. A device as defined in claim 1, wherein the scent-emitting substance includes one or more of orange, peppermint, lavender or sandalwood.

5. A device as defined in claim 1, wherein a surface of one or more of the pad, the label or the pouch is colored to indicate a scent of the scent-emitting substance.

6. A device as defined in claim 5, wherein one or more of (i) the scent of the scent-emitting substance includes one or more of orange or peppermint, and the color includes orange, or (ii) the scent includes one or more of lavender or sandalwood, and the color includes lavender.

7. A device as defined in claim 1, wherein the pad comprises a first relatively rough side for carrying a dye and a second relatively soft side disposed toward the label.

8. A device as defined in claim 1, wherein the sealed pouch includes at least one notch or frangible portion disposed thereon configured to facilitate cutting or tearing a portion of the sealed pouch to expose the pad to ambient air.

9. A device as defined in claim 1, wherein the sealed pouch includes a plurality of said at least one notch or frangible portion, each of said plurality configured to facilitate cutting or tearing a differently-sized portion of the sealed pouch to expose a differently-sized portion of the pad to ambient air.

10. A device as defined in claim 9, wherein each differently-sized portion of the pad emits a different amount, level or strength of scent from the at least one scent-emitting substance into the ambient air.

11. A device as defined in claim 1, wherein the scent-emitting substance is adapted to induce a physiological effect on a user to which the tab is attached including one or more of (i) relief from nausea or (ii) calming.

12. A device as defined in claim 1, wherein the liner further comprises perforations disposed between adjacent tabs.

13. A device as defined in claim 1, wherein the label comprises a foam.

14. A device as defined in claim 1, wherein each pad is sealed within a respective pouch, a first portion of the pouch is attached to the label, and a second portion of the pouch is unattached to the label to allow the pouch to be opened and expose the pad to ambient air.

15. A device as defined in claim 14, wherein the pouch is configured to be opened by cutting or tearing.

16. A device as defined in claim 1, wherein each label is adhesive backed for releasable attachment to a user.

17. A device as defined in claim 1, wherein each pad is an absorbent pad including thereon the scent-emitting substance, the pouch comprises plastic material, the absorbent pad is sealed within the plastic pouch, and the plastic pouch is fixedly connected on one end thereof to the label and is not connected to the label at another end of the pouch.

18. A scent-emitting tab comprising:
    a backing;
    a sealed pouch disposed on the backing;
    a scent-emitting substrate disposed within the sealed pouch; and
    adhesive for releasably attaching the backing to a user or article.

19. A scent-emitting tab as defined in claim 18, wherein the substrate is sealed within the pouch, a first end of the pouch is connected to the backing, and a portion of the pouch is free of the backing to allow the pouch to be opened and expose the scent-emitting substrate to ambient air.

20. A scent-emitting tab as defined in claim 19, wherein the pouch is configured to be opened by cutting or tearing.

21. A scent-emitting tab as defined in claim 18, wherein the backing includes the adhesive.

22. A scent-emitting tab as defined in claim 18, wherein a surface of one or more of the substrate, the backing or the pouch is colored to indicate a scent of the scent-emitting substance.

23. A scent-emitting tab comprising first means for releasably attaching the tab to a user or article; second means for emitting a scent; and third means for sealing the second means from ambient air until ready for use; wherein the first means comprises a label or backing.

24. A scent-emitting tab as defined in claim 23, wherein the label or backing comprises foam, the second means is an absorbent pad including thereon a scent-emitting substance, and the third means is a sealed pouch configured to be opened to expose the pad to ambient air.

25. A scent-emitting tab as defined in claim 23, further including fourth means for visually indicating the scent of the second means.

26. A scent-emitting tab as defined in claim 25, wherein the fourth means is a colored portion of one or more of the first, the second or the third means colored to indicate the scent.

27. A method comprising the following steps:
releasably attaching a scent-emitting tab to a user or article, the scent-emitting tab comprising a backing, the backing having disposed thereon an openable sealed pouch including a scent-emitting substrate therein including a scent, the scent-emitting tab further comprising adhesive for releasably attaching the backing to the user or article, the attaching step including attaching the backing to the user or article; and
opening the pouch, thereby exposing the scent-emitting substrate to ambient air to allow emitting of the scent into the ambient air.

28. A method as defined in claim 27, wherein the pouch comprises a first end connected to the backing and a second end not connected to the backing, and the opening step comprises opening the pouch at the second end or at a point between the first end and the second end.

29. A method as defined in claim 28, wherein the opening step comprises at least partially separating the second end from the first end.

30. A method as defined in claim 27, wherein the attaching step comprises releasably attaching the backing to an upper chest area of a patient prior to beginning a medical procedure.

31. A method as defined in claim 27, wherein the scent is adapted to induce a physiological effect on a patient and the attaching step comprises releasably attaching the backing to a patient prior to beginning a medical procedure for inducing the physiological effect on the patient with the scent.

32. A method as defined in claim 31, wherein the physiological effect is one or more of (i) relief from nausea or (ii) calming.

33. A method as defined in claim 31, wherein the medical procedure is a mammogram, an MRI, an imaging procedure, a needle injection, or an IV procedure, and further comprising performing the medical procedure after the physiological effect is induced.

34. A method as defined in claim 27, further comprising selecting the scent from a plurality of different scents prior to the step of releasably attaching the backing with the scent selected to the user or article.

35. A method as defined in claim 34, wherein the selecting step comprises selecting the scent based upon the desires of the patient.

36. A method as defined in claim 27, wherein the pouch includes at least one notch or frangible portion disposed thereon configured to facilitate cutting or tearing a portion of the pouch to expose the substrate to then ambient air, and the opening step comprises cutting or tearing the pouch at the notch or frangible portion.

37. A method as defined in claim 36, wherein the pouch includes a plurality of said at least one notch or frangible portion, each of said plurality configured to facilitate cutting or tearing a differently-sized portion the of the sealed pouch to expose a differently-sized portion of the substrate to the ambient air, and the opening step comprises one of a) cutting or tearing the pouch at a first of said plurality to emit a first amount, level or strength of scent into the ambient air; or b) cutting or tearing the pouch at a second of said plurality to emit a second amount, level or strength of scent into the ambient air that is different than the first amount, level or strength.

38. A method as defined in claim 36, wherein the pouch includes a plurality of said at least one notch or frangible portion, each of said plurality configured to facilitate cutting or tearing a differently-sized portion the of the sealed pouch to expose a differently-sized portion of the substrate to the ambient air, the opening step comprises cutting or tearing the pouch at a first of said plurality to expose a first-sized portion of the substrate to the ambient air, and the method further comprises, subsequent to the opening step, cutting or tearing the pouch at a second of said plurality to expose a second-sized portion of the substrate to the ambient air.

* * * * *